United States Patent
Becker et al.

(10) Patent No.: US 6,803,563 B2
(45) Date of Patent: Oct. 12, 2004

(54) METHOD AND APPARATUS FOR MONITORING THE QUALITY OF LUBRICANT

(75) Inventors: Edwin Becker, Reken (DE); Mark Zundel, Duisburg (DE)

(73) Assignee: Flender Service GmbH (DE)

( * ) Notice: Subject to any disclaimer, the term of this patent is extended or adjusted under 35 U.S.C. 154(b) by 0 days.

(21) Appl. No.: 10/737,243

(22) Filed: Dec. 16, 2003

(65) Prior Publication Data

US 2004/0124349 A1 Jul. 1, 2004

Related U.S. Application Data

(63) Continuation of application No. 10/633,265, filed on Aug. 1, 2003.

(30) Foreign Application Priority Data

Aug. 2, 2002 (DE) .......................... 102 35 612

(51) Int. Cl.$^7$ .......................... B01D 54/44; H01J 49/00; G01N 33/06
(52) U.S. Cl. ...................... 250/282; 250/286; 73/53.05; 73/54.02
(58) Field of Search ................................ 250/282, 286; 73/53.04, 54.02

(56) References Cited

U.S. PATENT DOCUMENTS

| | | | |
|---|---|---|---|
| 5,194,910 A | * | 3/1993 | Kirkpatrick et al. .......... 356/70 |
| 5,719,392 A | | 2/1998 | Franzen |
| 5,817,928 A | * | 10/1998 | Garvey et al. ............. 73/53.05 |
| 5,889,683 A | * | 3/1999 | Ismail et al. ................. 700/272 |
| 6,032,100 A | | 2/2000 | Forfitt et al. |
| 6,175,111 B1 | | 1/2001 | Sorita et al. |
| 6,225,623 B1 | | 5/2001 | Turner et al. |
| 6,421,588 B1 | | 7/2002 | Janata |
| 6,452,179 B1 | * | 9/2002 | Coates et al. .......... 250/339.09 |
| 6,455,850 B1 | * | 9/2002 | Coates et al. ............ 250/338.1 |
| 6,582,661 B1 | * | 6/2003 | Pardue et al. .............. 422/68.1 |
| 6,657,197 B2 | * | 12/2003 | Droessler et al. ...... 250/339.12 |

FOREIGN PATENT DOCUMENTS

| | | |
|---|---|---|
| DE | 39 04 142 | 8/1990 |
| DE | 39 31 497 | 4/1991 |
| DE | 41 26 927 | 8/1992 |
| DE | 19515270 | 11/1996 |
| DE | 196 50 397 | 6/1998 |
| DE | 199 33 924 | 11/2000 |
| EP | 0 672 243 | 3/2000 |
| WO | WO 95/00833 | 1/1995 |
| WO | WO 96/18893 | 6/1996 |
| WO | WO 98/53296 | 11/1998 |
| WO | WO 01/73816 | 1/2001 |

OTHER PUBLICATIONS

XP–002253739, Article by Dianne M. Levermore.
XP–002253740, Article by Thomas Fruh.
XP–002253741, Article by Dipl.–Ing. F. Plenert.

* cited by examiner

*Primary Examiner*—John R. Lee
*Assistant Examiner*—Kalimah Fernandez
(74) *Attorney, Agent, or Firm*—R. W. Becker & Associates; Robert W. Becker

(57) ABSTRACT

A method and apparatus are provided for monitoring the quality of lubricant that is in a gear mechanism or machine that contains effective materials. A sample of the lubricant or of the vapor that escapes from the lubricant is withdrawn from the gear mechanism or machine. The sample is conveyed to an ion mobility spectrometer, where materials present in the vapor phase above the lubricant are analyzed. The change of the content and of the type of the analyzed materials in the sample is utilized as the actual condition for the aging of the lubricant.

9 Claims, 1 Drawing Sheet

METHOD AND APPARATUS FOR MONITORING THE QUALITY OF LUBRICANT

CROSS-REFERENCE TO RELATED APPLICATIONS

This application is a continuation of pending application Ser. No. 10/633,265 filed on Aug. 1, 2003.

BACKGROUND OF THE INVENTION

The present invention relates to a method and to an apparatus for monitoring the quality of lubricating oil (hereinafter also designated merely as lubricant) that is in a gear mechanism or a machine and that contains effective materials or substances.

In machinery and equipment construction, and in particular in gear mechanism technology, the quality of the lubricant is an important influencing factor that determines the availability, the reliability and the safety of the overall drive train or the lubricated structural components. Oil-soluble effective substances, such as, for example, various extreme-pressure and anti-wear additives, are added to mineral oils, mineral oil products, or synthetic oils to improve the lubricating effect or the chemical properties. Differences in the quality in the various lubricants represents a competitive criterion. Experience in the maintenance of gear mechanisms has shown that even the best lubricants age and must be exchanged. In this connection, one changes over in stages from the scheduled oil change intervals more to oil change periods that are a function of the condition of the oil or lubricant. The criterion is the classic oil analysis by means of which the physical and chemical parameters of the lubricant are analyzed.

Unfortunately, clearly measurable criteria that can be a measure of when the quality of an oil is insufficient, do not yet exist. For this reason, for example in the wind power industry, it is a standard and required by regulation, that for wind power units the towers must be regularly climbed, oil samples taken, and the oil quality subsequently determined in a laboratory. If individual parameters of the oil become impaired, the lubricant is exchanged already for safety reasons. To be able to determine the suitable point in time for changing the oil, these analyses require a well-equipped analysis laboratory, as well as a precise withdrawal of sample. Determined are the viscosity, the pH, the quantity of foreign particles, and their composition. The properties can be determined only with very expensive analysis equipment, and can be evaluated only by specialists.

Immediate indications of possible danger to the gear mechanism due to an inadequate quality of the aged oil are possible only in the final stage of the lubricant. A large number of oil-changing criteria can be found in the technical literature; these criteria in part contradict one another.

It is therefore an object of the present invention to provide a method and an apparatus that, on site, enables a rapid and reliable monitoring of the quality of the lubricant in a gear mechanism or machine.

BRIEF DESCRIPTION OF THE DRAWINGS

This object, and other objects and advantages of the present invention, will appear more clearly from the following specification in conjunction with the single schematic drawing, which shows a diagrammatic view of one exemplary embodiment of an inventive apparatus for monitoring the lubricant quality.

SUMMARY OF THE INVENTION

Figure 1:
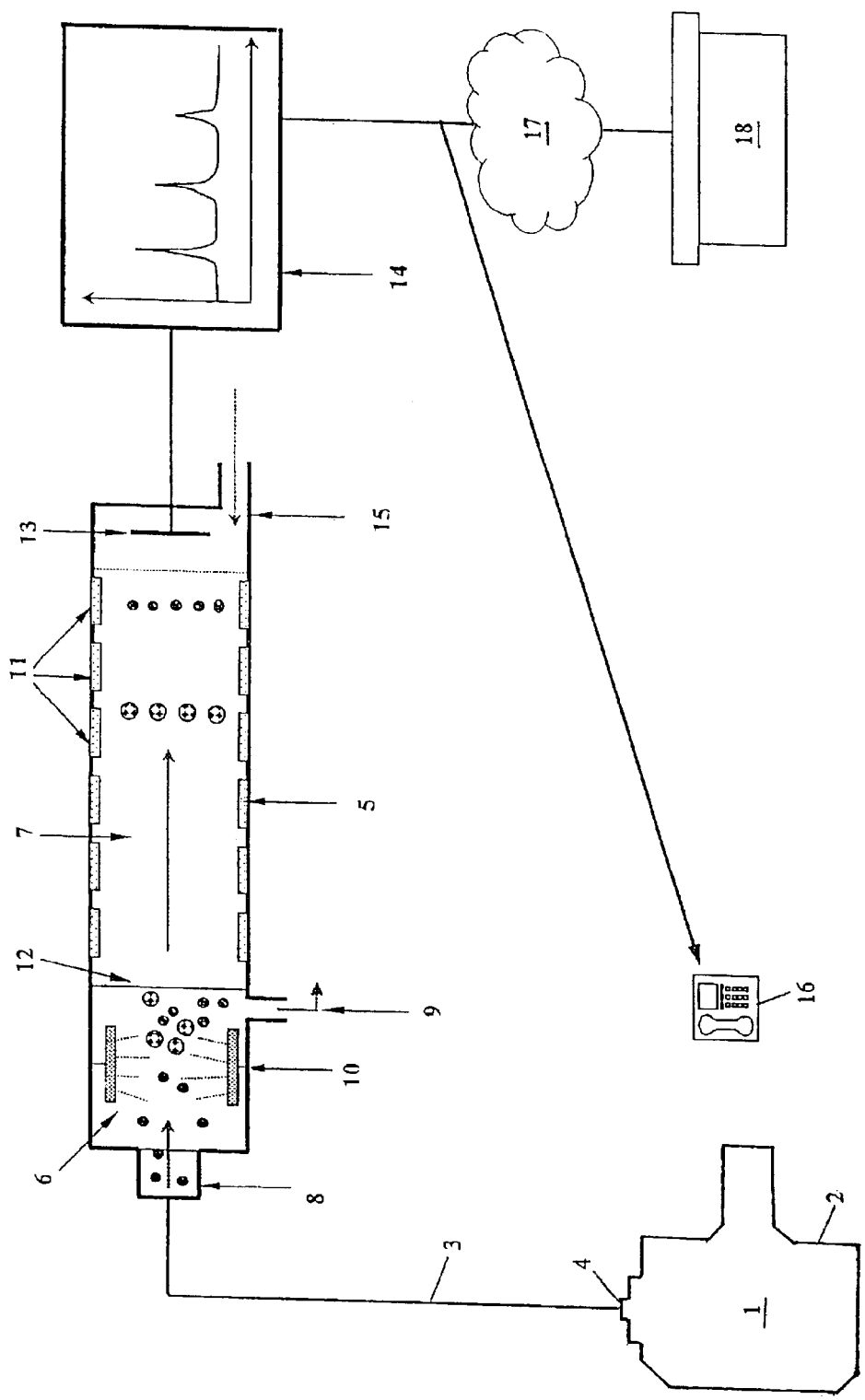

The inventive method of monitoring the quality of lubricant includes the steps of withdrawing from a gear mechanism or machine a sample of the lubricant or of vapor that escapes from the lubricant, conveying a sample of the vapor escaping from the lubricant to an ion mobility spectrometer, analyzing materials of the sample that are present in a vapor phase above the lubricant, and comparing a change of content and type of analyzed materials in the sample to predetermined materials in a vapor phase of virgin lubricant, and using such comparison as an actual condition for the aging of the lubricant.

The inventive apparatus for monitoring the quality of the lubricant comprises a sample withdrawal line connected to the gear mechanism or machine, an ion mobility spectrometer connected to the sample withdrawal line, and an analysis unit connected to the ion mobility spectrometer.

The inventive approach is based on the recognition by the inventor of the fact that the lubricants can be differentiated by their odor depending upon origin, age and composition. The odor results, among other things, from the effective materials and their decomposition products that are added to the heavy-duty lubricants to improve the properties thereof. If the content of the effective materials in the lubricant is reduced during operation due to aging, the composition of the vapor phase over the lubricant also changes. Pursuant to the present invention, it is now proposed to analyze the materials present in the vapor phase above the lubricant with a measuring device, especially with an ion mobility spectrometer. An ion mobility spectrometer is known, for example, from DE 195 15 270 A, and is used for the analysis of trace gases. Within the context of the present invention, the ion mobility spectroscopy is used to analyze the materials present in the vapor phase above the oil and to compare the results with comparison values that are found in virgin lubricants. From the change of the content of volatile components relative to the starting condition, a conclusion is drawn of the changed quality of the lubricant. The type of determination of the state of the quality of the oil with the aid of the ion mobility spectrometer is reliable and rapid, can be carried out on site, and can be remotely controlled. The measurement results can be transmitted to any desired location, thereby enabling a remote monitoring.

Further specific features of the present invention will described in detail subsequently.

DESCRIPTION OF PREFERRED EMBODIMENTS

Referring now to the drawing in detail, the gear mechanism 1 or a machine is surrounded by a housing 2 that is filled to a prescribed level with lubricating oil or lubricant to lubricate the rotating parts within the housing 2. The gear mechanism 1 is preferably installed in a unit, for example in a wind power unit, that is not constantly monitored by personnel.

The housing 2 of the gear mechanism 1 is provided with a sample withdrawal line 3 by means of which a quantity of lubricant sample, or of oil vapor, which forms above the oil bath in the housing 2, is withdrawn. If oil vapor is withdrawn, the sample withdrawal line 3 can be connected to the oil-venting device 4 by means of which a pressure equalization is provided for the gear mechanism 1. The sample withdrawal line 3 can also be connected to a different connector that is mounted on the housing 2 above the oil bath.

The sample withdrawal line 3 is guided to a measuring device, especially an ion mobility spectrometer 5, which comprises a reaction chamber 6 and a drift chamber 7. The reaction chamber 6 is provided with a sample inlet 8 and an outlet 9, and accommodates an ionization source 10. The drift chamber 7 is provided on the inner side with drift rings 11 that are connected in pairs and are connected with a high voltage direct current source. As a result, an axial electrostatic field is built up in the drift chamber 7.

The reaction chamber 6 is separated from the drift chamber 7 by a switching or contact grid 12 that in principle is provided with a plurality of electrically conductive elements that are connected in pairs and are connected to a power source. The elements are separated from one another by openings or perforations. At that end opposite the contact grid 12, an ion detector 13 is disposed in the drift chamber 7. The ion detector 13 is connected via an amplifier with an analysis unit 14, which in turn can be connected with a remote monitoring site.

In the reaction chamber 6, the molecules contained in the entering sample stream are ionized with the aid of the ionization source 10. By applying a specified voltage pattern, the contact grid 12 is alternatingly open or blocked for the ions. In the open phase, the ions enter the drift chamber 7, where they are separated and migrate in the direction toward the ion detector 13 against a drift gas, for example air, nitrogen or the like, that has been supplied via the drift gas inlet 15. The ions that strike or encounter the ion detector 13 cause, at that location, a signal stream that is stored and analyzed in the analysis unit 14. Depending upon the content or the type of material that is to be tested, different spectra result in the analysis unit 14.

The materials contained in the oil vapor are analyzed pursuant to the process principle described above, whereby depending upon the content of the type of materials, a specific spectrum is given that is indicated in the analysis unit 14. Since various effective materials or substances are added to a lubricant, the decomposition products that are contained in the oil vapor and are clearly shown in the analyzed spectrum represent a significant index for the condition of the lubricant. If the appearance of the spectra (actual condition) changes in comparison with the starting condition (desired condition) of the virgin lubricant, it is possible to determine with the aid of the pertaining spectra how the additive of the lubricant that is important for operation has decomposed, and if the lubricant has aged or even contains water.

The measurement results obtained by the ion mobility spectrometer 5 with regard to the change in the content and the type of the materials contained in the oil vapor are utilized in the analysis unit 14 as the actual condition for the aging of the lubricant relative to virgin lubricant. When a prescribed threshold is reached or exceeded in the analysis unit 14, a warning signal is generated, for example for the maintenance personnel. The analyzed measurement results can also be transmitted to the maintenance personnel via known telediagnostic technology.

As a result of the analysis, an alarm can be triggered in a control room 16. The measurement results can also be conveyed to a remote data transmission means 17, e.g. telemetry, or the internet, and can be recalled in a remote monitoring station 18. If from the analyzed and transmitted measurement results there is indicated a critical condition with regard to the quality of the lubricant, there is a requirement for action, which is indicated to the maintenance personnel by a warning signal. Then, if necessary, fresh effective material is added to the aged lubricant, or the lubricant is exchanged.

The specification incorporates by reference the disclosure of German priority document 102 35 612.2 filed Aug. 2, 2002.

The present invention is, of course, in no way restricted to the specific disclosure of the specification and drawing, but also encompasses any modifications within the scope of the appended claims.

What is claimed is:

1. A method of monitoring the quality of lubricant that is in a gear mechanism or machine and that contains effective materials, said method including the steps of:
    withdrawing from the gear mechanism or machine a sample of said lubricant or of vapor that escapes from said lubricant,
    conveying a sample of the vapor escaping from the lubricant to an ion mobility spectrometer,
    analyzing materials of said sample that are present in a vapor phase above said lubricant, and
    comparing a change of content and type of analyzed materials in said sample to predetermined materials in a vapor phase of virgin lubricant, and using such comparison as an actual condition for an aging of said lubricant.

2. A method according to claim 1, wherein the lubricant is classified pursuant to the analysis of the determined measurement results by comparison with prescribed threshold values.

3. A method according to claim 1, wherein after the analysis of the determined measurement results by comparison with prescribed threshold values, effective materials are added to the lubricant.

4. A method according to claim 1, wherein after the analysis of the determined measurement results by comparison with prescribed threshold values, the lubricant is exchanged.

5. An apparatus for monitoring the quality of lubricant that is in a gear mechanism or machine and that contains effective materials, said apparatus comprising
    a sample withdrawal line connected to said gear mechanism or machine,
    an ion mobility spectrometer connected to said sample withdrawal line, and
    an analysis unit connected to said ion mobility spectrometer.

6. An apparatus according to claim 5, wherein said analysis unit is connected to a control room.

7. An apparatus according to claim 5, wherein said analysis unit is connected to a remote monitoring station.

8. An apparatus according to claim 5, wherein said sample withdrawal line is connected to an inner chamber of said gear mechanism or machine above a level of said lubricant therein.

9. An apparatus according to claim 5, wherein said gear mechanism or machine is provided with an oil-venting device, and wherein said sample withdrawal line is connected to said oil-venting device.

* * * * *